United States Patent
Huang

(10) Patent No.: US 8,546,585 B2
(45) Date of Patent: Oct. 1, 2013

(54) PROCESS FOR PREPARING EPROSARTAN MESYLATE

(75) Inventor: Xiangliang Huang, Linhai (CN)

(73) Assignee: Zhejiang Huahai Pharmaceutical Co., Ltd., Linhai, Zhejiang (CN)

( * ) Notice: Subject to any disclaimer, the term of this patent is extended or adjusted under 35 U.S.C. 154(b) by 442 days.

(21) Appl. No.: 12/989,765

(22) PCT Filed: Jul. 20, 2009

(86) PCT No.: PCT/CN2009/072832
§ 371 (c)(1),
(2), (4) Date: Oct. 26, 2010

(87) PCT Pub. No.: WO2010/015169
PCT Pub. Date: Feb. 11, 2010

(65) Prior Publication Data
US 2011/0046391 A1 Feb. 24, 2011

(30) Foreign Application Priority Data
Aug. 3, 2008 (CN) .......................... 2008 1 0129646

(51) Int. Cl.
*C07D 233/64* (2006.01)
(52) U.S. Cl.
USPC ....................................................... 548/315.1
(58) Field of Classification Search
USPC ....................................................... 548/315.1
See application file for complete search history.

(56) References Cited

U.S. PATENT DOCUMENTS
5,185,351 A 2/1993 Finkelstein et al. .......... 514/341

FOREIGN PATENT DOCUMENTS
| WO | WO 97/36874 A1 | 10/1997 |
| WO | WO 2008/078330 A1 | 7/2008 |
| WO | 2009/013760 | 1/2009 |
| WO | WO 2009/084028 A2 | 7/2009 |

OTHER PUBLICATIONS

European Search Report and Written Opinion, dated Aug. 4, 2011, for EPAN 09804469.6, 6 pages.
Serajuddin, "Salt formation to improve drug solubility," *Advanced Drug Delivery Reviews* 59:603-616, 2007.
Snodin, "Residues of genotoxic alkyl mesylates in mesylate salt drug substances: Real or imaginary problems?," *Regulatory Toxicology and Pharmacology* 45:79-90, 2006.

*Primary Examiner* — Jason M Nolan
(74) *Attorney, Agent, or Firm* — Seed IP Law Group PLLC

(57) ABSTRACT

The present invention discloses a process for preparing eprosartan mesylate, in which eprosartan is dissolved or suspended in glacial acetic acid, then methanesulfonic acid is added and a solution of eprosartan mesylate in glacial acetic acid is obtained by stirring, a solid of eprosartan mesylate is precipitated by continuously stirring and then obtained by filtration, or a solid of eprosartan mesylate is obtained by concentrating the glacial acetic acid to dry, or a solid of eprosartan mesylate is obtained by adding dropwise an organic ester solvent into the glacial acetic acid under stirring to precipitate a crystal and separate the crystal.

13 Claims, No Drawings

PROCESS FOR PREPARING EPROSARTAN MESYLATE

The present application claims the priority of China application No. 200810129646.4, filed with the State Intellectual Property Office on Aug. 3, 2008, titled "a new salifying process for eprosartan mesylate", and the entirety thereof is incorporated herein by reference.

TECHNICAL FIELD

The present invention relates to a salifying process for a drug compound, eprosartan mesylate, and pertains to the field of medicine and chemistry.

BACKGROUND ART

Eprosartan mesylate was developed successfully by SmithKline Beecham Corporation in 1997, and marketed in Germany in 1998 under the trade-name Teveten and in the United States later in 1999. Eprosartan mesylate, as an angiotensin II receptor blocker, is an antihypertensive drug of the latest generation. Eprosartan mesylate is potent to lower systolic and diastolic pressures in mild, moderate and severe hypertensive patients, and is safe and tolerable. Eprosartan mesylate is rapidly absorbed when administrated orally, with a bioavailability of 13% and a protein binding rate of 98%. The blood peak concentration and AUC (Area Under Curve) can be elevated by about 50% in patients with liver and kidney dysfunction, or fullness after administration, and can be elevated by 2 to 3 folds in elderly patients. Eprosartan mesylate has a structure shown as follows:

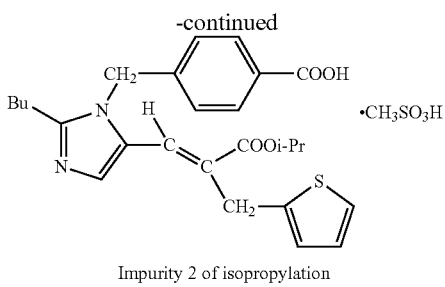

Eprosartan Mesylate

U.S. Pat. No. 5,185,351 discloses a method for preparing eprosartan mesylate using Eprosartan and methanesulfonic acid in isopropanol (U.S. Pat. No. 5,185,351, Example 41 (ii)). However, it is found when following this method for preparing eprosartan mesylate in industry, an esterification reaction can occur between eprosartan and isopropanol and the following two impurities can be generated:

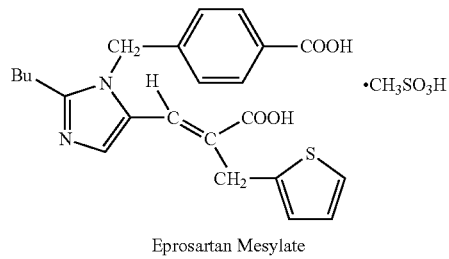

Impurity 1 of isopropylation

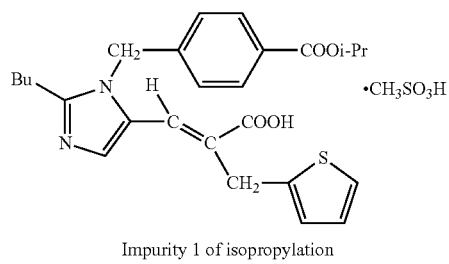

Impurity 2 of isopropylation

In addition to the above two esterification impurities, the salifying method provided by the above patent is prone to produce isopropyl mesylate. Considering currently known potential risk of gene toxicity of methylsulfonic acid ester on human as well as the stringent requirements of methylsulfonic acid ester from the Europe and the America authorities, it is important to produce eprosartan mesylate in a non-alcohol solvent during the process of producing eprosartan mesylate, since it avoids the formation of methylsulfonic acid ester and the residue thereof in the final product. Since the dosage of eprosartan mesylate is high, it is particularly important to strictly control methylsulfonic acid ester in eprosartan mesylate.

In addition, for the above salifying method, solid eprosartan is suspended in propanol at a low temperature, then methanesulfonic acid is added, about ten seconds later a great deal of eprosartan mesylate precipitate is obtained. Therefore, solid eprosartan may be embedded by the precipitated eprosartan mesylate. Since isopropyl alcohol has a high viscosity at low temperature, a heavy filtering operation burden is needed to obtain solid from isopropanol, and the obtained solid contains quite an amount of isopropanol.

SUMMARY OF THE INVENTION

The present invention overcomes the problem of production of impurities isopropyl mesylate and eprosartan isopropyl ester during the preparation of eprosartan mesylate, and provides a process for preparing eprosartan mesylate that is easy to handle, suitable for industrial production, economic, effective and with high yield and high purity.

After numerous trials, the inventor found that: eprosartan was suspended or dissolved in glacial acetic acid, then methanesulfonic acid was added to obtain a clear solution of eprosartan mesylate in glacial acetic acid; after about 1 hour of stirring, eprosartan mesylate solid would precipitate slowly, and thus the salification of eprosartan with methanesulfonic acid avoids embedment; ethyl acetate was added to render eprosartan mesylate crystallized completely, the obtained solid was easy to filter and drain under a reduced pressure, the wet product obtained had a low solvent content and thus was easy to dry. In addition, the new process of adding methanesulfonic acid into a solution of eprosartan in acetic acid did not produce new impurities, and the originally existing impurities decreased by some extent.

An embodiment of the present invention is as follows: eprosartan is dissolved or suspended in glacial acetic acid, then methanesulfonic acid is added and stirred to obtain a solution of eprosartan mesylate in glacial acetic acid, the precipitated solid is stirred and filtered to obtain a solid of eprosartan mesylate, or glaicial acetic acid is concentrated to dry to obtain a solid of eprosartan mesylate, or an organic ester solvent is added dropwise to the glacial acetic acid under stirring to precipitate crystal and separate to obtain a solid of eprosartan mesylate, wherein the ratio of eprosartan (mass, g): methanesulfonic acid (mass, g): glacial acetic acid (volume, ml) is 1:0.1-5.0:1-15, and the temperature of reaction is 10° C.-110° C.

The reaction scheme of the present invention is as follows:

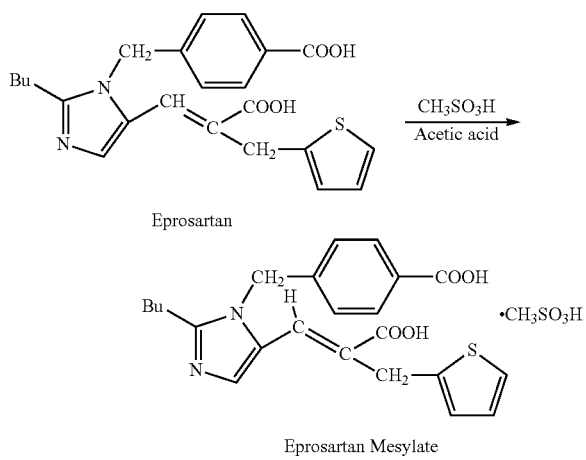

In the present invention, eprosartan can be suspended in glacial acetic acid, or be heated to partly or totally dissolved in glacial acetic acid, then methanesulfonic acid is added. Preferably, eprosartan is suspended in glaicial acetic acid and then methanesulfonic acid is added.

In the reaction of the present invention, the ratio of the amount of glacial acetic acid (ml) to the mass of eprosartan (g) is preferably 3-4 ml/g. The ratio of the amount of eprosartan (g) to methanesulfonic acid (g) is preferably 1:0.3-0.5.

In the present invention, the temperature of salifying reaction with methanesulfonic acid is 10° C. to 110° C., preferably 25° C. to 35° C.; the duration of reaction is 5 minutes to 3 hours, preferably 0.5-1 hour.

The method for separating eprosartan mesylate in the present invention comprises: continuously stirring to precipitate solid, and filtering to obtain a solid of eprosartan mesylate; or concentrating glacial acetic acid to dry and then washing with an organic ester solvent; or adding dropwise an organic ester solvent into glacial acetic acid under stirring to precipitate eprosartan mesylate and then separating to obtain a solid of eprosartan mesylate, wherein the added organic ester solvent is a C3-C10 ester, such as ethyl acetate, isopropyl acetate or tert-butyl acetate, the amount thereof is 1-30 times of the mass of eprosartan (ml/g), preferably 6-8 times (ml/g); and the preferable solvent is ethyl acetate.

The recommended preparation method is as follows: suspending eprosartan in glacial acetic acid of an amount of 3-4 times of eprosartan (ml/g), stirring at room temperature for 5-10 minutes, then adding methanesulfonic acid of an amount of 0.3 times of eprosartan (g/g) to obtain a clear solution immediately, keeping the stirring for about further one hour, adding dropwise ethyl acetate of an amount of 6-8 times of eprosartan (ml/g), keeping the stirring for further 3-5 hours after adding, filtering under a reduced pressure, and drying under a vacuum at 50° C. to obtain an off-white solid of eprosartan mesylate.

The present invention has the following advantages over the prior art:
1. The isopropyl ester impurity, which is generated from the salifying process of the prior art and is difficult to be removed by recrystallization in the subsequent procedure, is avoided;
2. The isopropyl mesylate does not generated in the process of the present invention, and thus the final product does not contain isopropyl mesylate impurity;
3. The process of the present invention is simple to operate and has a stable yield, furthermore, the product thereof is easy to dry;
4. The product obtained by the process of the present invention has a high purity and meets the requirement of final product without further purification.

SPECIFIC MODELS FOR CARRYING OUT THE PRESENT INVENTION

The embodiments of the present invention are further illustrated in the following specific examples, but the scope of the present invention is not limited to them.

EXAMPLE 1

To a 500 ml flask was added 31.8 g of eprosartan and 128 mL of glacial acetic acid, stirred for 10 minutes at room temperature, then 9.4 g of methanesulfonic acid was added, the reaction solution became clear quickly and was stirred for about one more hour, then a white solid precipitated, the reaction was stirred for about 5 more hours, filtered under reduced pressure, dried in vacuum at 50° C., and an off-white solid was obtained (22.6 g, yield 58%).

EXAMPLE 2

To a 500 ml flask was added 31.8 g of eprosartan and 222 mL of glacial acetic acid, heated to 75° C. under stirring to get a clear solution, 10.8 g of methanesulformic acid was added, stirred for 2 more hours, cooled, concentrated to dry, and 300 ml of isopropyl acetate was added, stirred for 3 hours at room temperature, filtered under reduced pressure, dried in vacuum at 50° C., and an off-white solid was obtained (34.9 g, yield 89.5%).

EXAMPLE 3

To a 500 ml flask was added 31.8 g of eprosartan and 222 mL of glacial acetic acid, heated to 75° C. under stirring to get a clear solution, 10.8 g of methanesulformic acid was added, stirred for one more hour, cooled to room temperature, and 300 ml of n-butyl acetate was added dropwise, stirred for 3 hours at room temperature after adding, filtered under reduced pressure, dried in vacuum at 50° C., and an off-white solid was obtained (32.7 g, yield 83.9%).

EXAMPLE 4

To a 500 ml flask was added 31.8 g of eprosartan and 128 mL of glacial acetic acid, heated to reflux at 110° C., stirred to get a clear solution, cooled, 9.4 g of methanesulformic acid was added, stirred for 2 more hours, cooled, concentrated to dry, and 300 ml of ethyl acetate was added, stirred for 3 hours at room temperature, filtered under reduced pressure, dried in vacuum at 50° C., and an off-white solid was obtained (34.0 g, yield 87.2%).

EXAMPLE 5

To a 500 ml flask was added 31.8 g of eprosartan and 128 mL of glacial acetic acid, stirred for 10 minutes at room temperature, then 9.4 g of methanesulfonic acid was added, the reaction solution became clear quickly and was stirred for 2 more hours, concentrated to dry, and 200 ml of ethyl acetate was added, stirred for 3 hours at room temperature, filtered under reduced pressure (wet weight: 35.6 g), dried in vacuum at 50° C., and an off-white solid was obtained (33.7 g, yield 86.4%) with a purity of 99.8%.

EXAMPLE 6

To a 500 ml flask was added 20.0 g of eprosartan and 80 mL of glacial acetic acid, stirred for 10 minutes at room temperature, then 5.9 g of methanesulfonic acid was added, the reaction solution became clear quickly and was stirred for 1 more hour, 200 ml of ethyl acetate was added, stirred for 3 hours at room temperature after adding, filtered under reduced pressure (wet weight: 19.6 g), dried in vacuum at 50° C., and an off-white solid was obtained (20.5 g, yield 83.7%) with a purity of 99.8%.

EXAMPLE 7

To a 1000 ml flask was added 25.0 g of eprosartan and 300 mL of glacial acetic acid, stirred for 10 minutes at room temperature, 9.4 g of methanesulfonic acid was added, stirred for one more hour, and 600 ml of ethyl acetate was added dropwise, stirred for 3 hours at room temperature, filtered under reduced pressure, dried in vacuum at 50° C., and an off-white solid was obtained (23.8 g, yield 76.8%).

EXAMPLE 8

To a 500 ml flask was added 25.0 g of eprosartan and 75 mL of glacial acetic acid, stirred for 10 minutes at room temperature, then 7.4 g of methanesulfonic acid was added, the reaction solution became clear quickly and was stirred for two more hours, 420 ml of ethyl acetate was added dropwise, stirred for 3 hours at room temperature, filtered under reduced pressure, dried in vacuum at 50° C., and an off-white solid was obtained (26.4 g, yield 86.0%) with a purity of 99.8%.

The embodiments of present invention are described in detail hereinbefore. Specific examples are applied to illustrate the principle and the embodiments of the present invention. The specific embodiments and the applied scope thereof may vary based on the principle of the present invention for those skilled in the art. Therefore, the contents recited herein should not be construed as limitation to the present invention.

What is claimed is:

1. A salifying process for preparing eprosartan mesylate, comprising:
    (i) dissolving or suspending eprosartan in glacial acetic acid,
    (ii) adding methanesulfonic acid to the mixture of step (i) to obtain a solution of eprosartan mesylate in glacial acetic acid, and
    (iii) (a) obtaining a solid of eprosartan mesylate by continuously stirring the solution of step (ii) to precipitate the solid and then separating the solid by filtration,
    (b) obtaining a solid of eprosartan mesylate by concentrating the glacial acetic acid to dry, or
    (c) obtaining a solid of eprosartan mesylate by adding dropwise an organic ester solvent into the glacial acetic acid under stirring to precipitate the solid and separate the solid.

2. The salifying process for preparing eprosartan mesylate according to claim 1, wherein eprosartan is suspended in glacial acetic acid or heated to be partly or totally dissolved in the glacial acetic acid, and then methanesulfonic acid is added.

3. The salifying process for preparing eprosartan mesylate according to claim 1, wherein eprosartan (mass, g): methanesulfonic acid (mass, g) : glacial acetic acid (volume, ml) is 1:0.1-5.0: 1-15.

4. The salifying process for preparing eprosartan mesylate according to claim 3, wherein the ratio of the mass of eprosartan (g) to the amount of glacial acetic acid (ml) is 1:3-4; and the ratio of the amount of eprosartan (g) to methanesulfonic acid (g) is 1:0.3-0.5.

5. The salifying process for preparing eprosartan mesylate according to claim 1, wherein the temperature of salifying reaction of methanesulfonic acid is 10° C.-110° C.

6. The salifying process for preparing eprosartan mesylate according to claim 1, wherein the reaction time after the addition of methanesulfonic acid is 5 minutes to 3 hours.

7. The salifying process for preparing eprosartan mesylate according to claim 1, wherein the added organic ester solvent is a C3-C10 ester.

8. The salifying process for preparing eprosartan mesylate according to claim 7, wherein the amount added of the organic ester solvent is 1-30 times of the mass of eprosartan (ml/g).

9. The salifying process for preparing eprosartan mesylate according to claim 2, wherein eprosartan is suspended in glacial acetic acid and then methanesulfonic acid is added.

10. The salifying process for preparing eprosartan mesylate according to claim 5, wherein the temperature of salifying reaction of methanesulfonic acid is 25° C.-35° C.

11. The salifying process for preparing eprosartan mesylate according to claim 6, wherein the reaction time after the addition of methanesulfonic acid is 0.5-1 hour.

12. The salifying process for preparing eprosartan mesylate according to claim 7, wherein the added organic ester solvent is ethyl acetate.

13. The salifying process for preparing eprosartan mesylate according to claim 8, wherein the amount added to the organic ester solvent is 6-8 times of the mass of eprosartan (ml/g).

* * * * *